(12) United States Patent
Kertser

(10) Patent No.: US 10,925,514 B2
(45) Date of Patent: Feb. 23, 2021

(54) SYSTEMS AND METHODS FOR CONCOMITANT $CO_2$ SAMPLING AND $O_2$ DELIVERY

(71) Applicant: ORIDION MEDICAL 1987 LTD., Jerusalem (IL)

(72) Inventor: Michael Kertser, Jerusalem (IL)

(73) Assignee: ORIDION MEDICAL 1987 LTD., Jerusalem (IL)

( * ) Notice: Subject to any disclaimer, the term of this patent is extended or adjusted under 35 U.S.C. 154(b) by 208 days.

(21) Appl. No.: 15/898,797

(22) Filed: Feb. 19, 2018

(65) Prior Publication Data

US 2018/0235511 A1     Aug. 23, 2018

Related U.S. Application Data

(60) Provisional application No. 62/461,121, filed on Feb. 20, 2017.

(51) Int. Cl.
    *A61B 5/083*     (2006.01)
    *A61M 16/12*     (2006.01)
    (Continued)

(52) U.S. Cl.
    CPC .......... *A61B 5/0836* (2013.01); *A61B 5/0833* (2013.01); *A61B 5/725* (2013.01);
    (Continued)

(58) Field of Classification Search
    CPC .. A61M 16/00; A61M 16/022; A61M 16/024; A61M 16/085; A61M 16/10; A61M 16/12; A61M 2016/1025; A61M 2016/103; A61M 2230/432; A61M 2230/435; A61M 2202/0208; A61M 2202/0225;
    (Continued)

(56) References Cited

U.S. PATENT DOCUMENTS 7,376,453 B1    5/2008    Diab et al.
2002/0082511 A1*   6/2002    Carlebach ............ A61B 5/0836
                                                        600/529

(Continued)

FOREIGN PATENT DOCUMENTS

WO      2016035035 A1    3/2016
WO      2016108127 A1    7/2016

OTHER PUBLICATIONS

International Search Report and Written Opinion for PCT Application No. PCT/IL2018/050183 dated May 25, 2018; 11 pgs.

*Primary Examiner* — Joseph D. Boecker
(74) *Attorney, Agent, or Firm* — Cantor Colburn LLP

(57) ABSTRACT

A $CO_2$ monitoring system provides oxygen ($O_2$) to a subject's mask with known characteristics. The $CO_2$ monitoring system receives, from the mask, gas samples including exhaled $CO_2$ diluted by $O_2$. The $CO_2$ monitoring system uses an adaptive noise canceller to cancel the diluting $O_2$ by using the known characteristics of the $O_2$ provided to the mask, the result of which process is restoration of the original concentration level of the $CO_2$ as exhaled by the subject into the mask.

19 Claims, 4 Drawing Sheets

(51) Int. Cl.
*A61B 5/00* (2006.01)
*A61M 16/08* (2006.01)
*A61M 16/10* (2006.01)

(52) U.S. Cl.
CPC ......... *A61B 5/7214* (2013.01); *A61M 16/085* (2014.02); *A61M 16/12* (2013.01); *A61M 2016/103* (2013.01); *A61M 2016/1025* (2013.01); *A61M 2202/0208* (2013.01); *A61M 2205/702* (2013.01); *A61M 2230/432* (2013.01)

(58) Field of Classification Search
CPC ............. A61M 2205/702; A61B 5/082; A61B 5/0833; A61B 5/0836; A61B 5/091; A61B 5/7214; A61B 5/725
See application file for complete search history.

(56) References Cited

U.S. PATENT DOCUMENTS

2007/0107728 A1* 5/2007 Ricciardelli ........... A61B 5/087
128/204.21
2017/0281051 A1* 10/2017 Evans ................ A61M 16/0069
2017/0368294 A1* 12/2017 Orr ................... A61M 16/1005

* cited by examiner

SYSTEMS AND METHODS FOR CONCOMITANT $CO_2$ SAMPLING AND $O_2$ DELIVERY

CROSS-REFERENCE TO RELATED APPLICATION

This application claims the benefit of U.S. Provisional Application No. 62/461,121, filed Feb. 20, 2017, the content of which is incorporated herein by reference in its entirety for all purposes.

TECHNICAL FIELD

The present disclosure generally relates to capnography systems for sampling carbon dioxide ($CO_2$) that is exhaled by a subject, and more specifically to methods and systems that enable reliable measuring of exhaled $CO_2$ despite dilution of the exhaled $CO_2$ by oxygen that is concomitantly provided to the subject.

BACKGROUND

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

A human respiratory cycle includes a sequence of events during which a subject inhales and exhales a given volume of air through the respiratory system. The respiratory system includes the lungs that, during breathing, take in oxygen and expel $CO_2$, a waste gas. An exchange of oxygen and $CO_2$ in the lungs can be evaluated, for example, by measuring oxygen saturation level in the blood and concentration of exhaled $CO_2$. After $CO_2$ is exhaled, another respiratory cycle begins with the next breath.

Normal levels of both blood oxygen saturation and concentration level of exhaled $CO_2$ can attest to the healthiness of the subject's respiratory system. For example, if one's blood oxygen saturation level is normal, there may still be respiratory dysfunction which is, or caused due, for example, to inability of body cells to use oxygen that is absorbed in the blood. In general, the higher the incompetence of body cells to exploit oxygen (and the more incompetent cells there are), the lower the concentration of the $CO_2$ that the subject exhales.

Face (respiration) masks for subjects suffering from, prone to, or susceptible to, breathing problems typically include an oxygen port for delivering oxygen to a subject at a designated rate, and a $CO_2$ port for drawing $CO_2$ samples of $CO_2$ exhaled by the subject. Conventional masks that include the two ports have drawbacks. One drawback is that the sampled $CO_2$ is diluted by oxygen that is delivered to the subject continuously. Diluting the $CO_2$ gas by the oxygen (or by any other gas for that matter) decreases the concentration level (the partial pressure) of the $CO_2$ sample, causing the $CO_2$ measurement to be below capnography standards and leading to inaccurate, or incorrect, $CO_2$ concentration measurement and, potentially, to wrong conclusions that may be reached by the caring medical staff regarding the true respiratory condition of the subject. As a result of this, the $CO_2$ sampling port is typically located in the face mask adjacent to the oral/nasal openings, making the wearability of the face mask uncomfortable to the patient.

While sampling $CO_2$ and delivering oxygen are beneficial, there are some drawbacks which are associated with the concomitant use of the two functions (e.g., in terms of $CO_2$ dilution). It would be, therefore, beneficial to have methods and systems that would facilitate both reliable measurement and analysis of $CO_2$ samples (e.g., enable accurate measurement of end-tidal $CO_2$ (Et$CO_2$) values) with high confidence (e.g., ±4 mmHg), and concomitant delivery of oxygen at required oxygen flow rates, for example at oxygen flow rates of up to 10 liters per minute (LPM), without compromising the $CO_2$ measurement reliability.

SUMMARY

A $CO_2$ monitoring system provides oxygen to a subject's mask with known characteristics, and the $CO_2$ monitoring system receives, from the mask, gas samples including exhaled $CO_2$ that is diluted by oxygen, and uses an adaptive noise canceller, or other methods, to cancel the diluting oxygen by using the known characteristics of the oxygen that is provided to the mask, the result of which process is restoration of the original concentration level of the $CO_2$ as (originally) exhaled by the subject into the mask.

BRIEF DESCRIPTION OF THE DRAWINGS

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. Of the accompanying figures.

DETAILED DESCRIPTION

Figure 1:
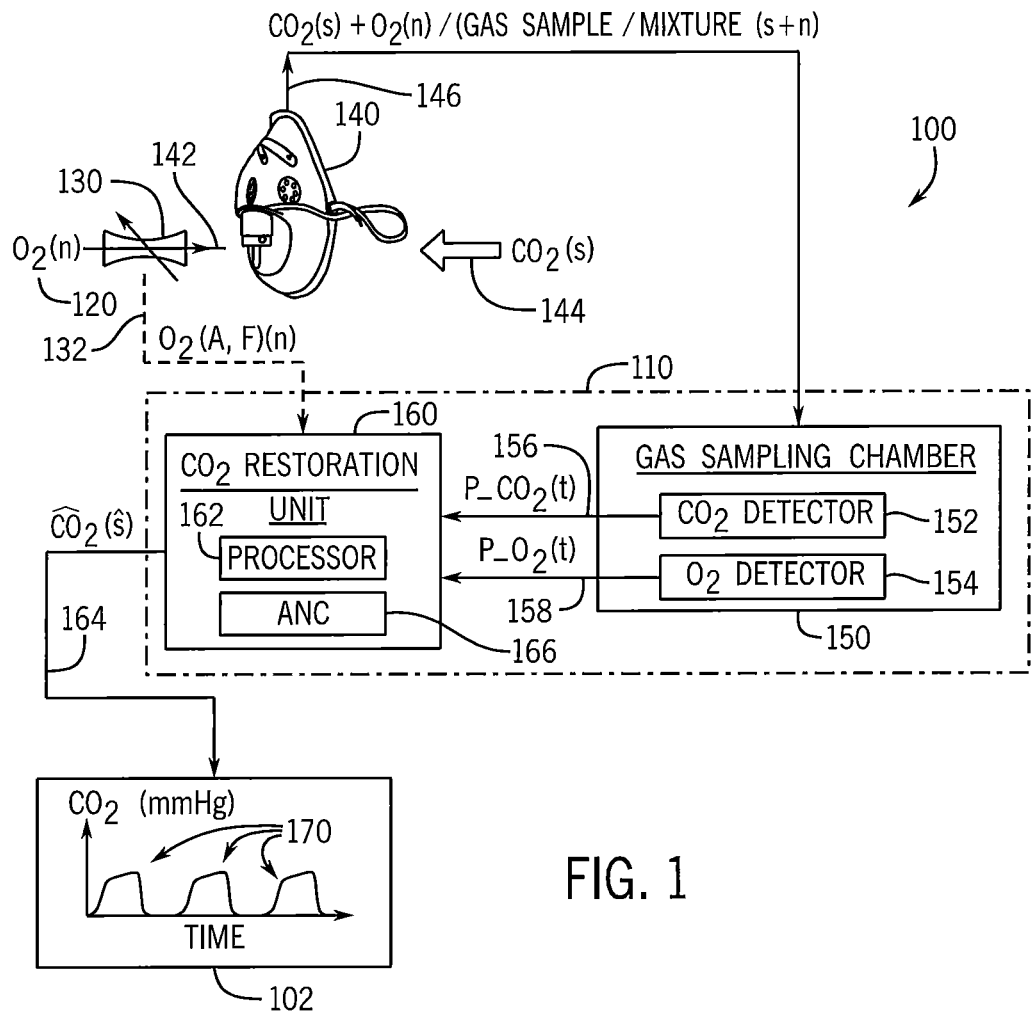
FIG. 1 shows a $CO_2$ monitoring system, according to an embodiment of the present disclosure.

The description that follows provides various details of exemplary embodiments. However, this description is not intended to limit the scope of the claims but instead to explain various principles of the disclosure and the manner of practicing it. Additionally, in an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but may nevertheless be a routine undertaking of design, fabrication, and manufacture for those of ordinary skill having the benefit of this disclosure. Further, the current embodiments may be implemented by one or more computer-processors that implement one or more machine-readable instructions stored on a tangible, non-transitory, machine-readable medium and/or by specialized circuitry designed to implement the discussed features.

The design of face masks (respiration masks) has generally been focused on the mechanical separation between oxygen flow and exhaled carbon dioxide ($CO_2$) in order to reduce the dilution of the exhaled $CO_2$ by oxygen ($O_2$). For example, certain masks include internal gas flow 'diversion' or 'separation' means (e.g., scoop, tubes, etc.) to divert one of the gas flows (e.g., exhaled $CO_2$ flow) in order to reduce the $CO_2$ dilution effect.

The present systems and methods enable use of a simplified ('basic') face mask, which may not include such means. Instead, exhaled $CO_2$ and $O_2$ that is provided to the mask are allowed to mix in the mask (e.g., the exhaled $CO_2$ is allowed to be diluted by $O_2$), but characteristics of the $O_2$ entering the mask (e.g., oxygen flow rate, pressure, amplitude, frequency, etc.) are known before it enters the mask. For example, the characteristics of the $O_2$ may be preset or measured in real-time before the $O_2$ enters the mask. By knowing the characteristics of the $O_2$ before it enters the mask, the oxygen 'noise' that dilutes the $CO_2$ samples may be decreased and, thus, the diluted $CO_2$ measurements (e.g., in terms of shape and amplitude) may be restored.

In a mixture of gases, each gas has a partial pressure, which is the hypothetical pressure of that gas if it alone occupied the entire volume of the original mixture at the same temperature. The total pressure of an ideal gas mixture is the sum of the partial pressures of each individual gas admixture in the gas mixture. The relationship between the volume of an individual gas (x) in a gas mixture and the gas partial pressure is shown below:

$$\frac{V_x}{V_{tot}} = \frac{p_x}{p_{tot}} = \frac{n_x}{n_{tot}}$$

where $V_x$ is the partial volume of the individual gas component (x), $V_{tot}$ is the total volume of the gas mixture, $p_x$ is the partial pressure of gas x, $p_{tot}$ is the total pressure of the gas mixture, $n_x$ is the amount of substance of gas x, and $n_{tot}$ is the total amount of substance in the gas mixture.

A concentration level of a first gas admixture in a two-gas mixture and a concentration level of a second gas admixture in the two-gas mixture are interrelated because, with a total pressure of the gas mixture assumed to be fixed, the greater the concentration of one gas admixture, the lower the concentration of the other gas admixture. The relationship between concentration (C) of an ideal gas in a gas mixture and partial pressure (P) of the ideal gas is given in the following formula:

$$P_A = C_A R T_A$$

where $C_A$ (=n/V) is a gas concentration (in moles per liter) at time A, n is number of moles of the solute, V is volume of the gas in liters, R is a gas constant, and T is temperature at time A.

This property of gases facilitates restoration of the concentration level of an oxygen-diluted exhaled $CO_2$. That is, by knowing a relationship between known characteristics (e.g., frequency and/or amplitude) of the $O_2$ originally provided to a respiration mask and measured characteristics of oxygen admixture in the $CO_2/O_2$ gas mixture, the measured concentration of the $CO_2$ admixture in the gas mixture may be restored to a value that is identical or similar to the $CO_2$ concentration level as (originally) exhaled by a subject. For example, the more the oxygen admixture in the $CO_2/O_2$ gas resembles the $O_2$ originally provided to a respiration mask, the lesser the extent by which the $CO_2$ concentration level has to be adjusted, or modified, in order to restore the original concentration level of the exhaled $CO_2$. On the other hand, the lesser the resemblance between the oxygen admixture in the $CO_2/O_2$ gas and the $O_2$ originally provided to a respiration mask, the greater the extent by which the $CO_2$ concentration level has to be adjusted or modified in order to restore the original $CO_2$ concentration level. That is, if the oxygen admixture significantly differs from the $O_2$ that is originally provided to the mask, this indicates that the oxygen admixture in the $CO_2/O_2$ gas mixture has been impacted by $CO_2$ having a relatively high concentration level. Therefore, restoring the exhaled $CO_2$ level may require a significant adjustment, or modification, of the measured $CO_2$ level.

Adaptive Noise Cancellers (ANCs) are known in the field of signal processing. Adaptive noise cancelling is an alternative method of estimating signals that are corrupted by additive noise or interference. An adaptive noise canceller uses a "primary" input containing the corrupted signal (in our case $CO_2$ signal that is corrupted by diluting $O_2$), and a "reference" input containing noise (in our case diluting $O_2$) correlated in some unknown way with the noise in the primary input. The reference input is adaptively filtered and subtracted from the primary input to obtain a signal estimate. When the reference input is free of signal noise and certain other conditions are met, noise in the primary input can be essentially eliminated without signal distortion. Some embodiments of the present disclosure use an ANC. Other embodiments may use alternative noise cancellation and signal estimation methods.

FIG. 1 shows a carbon dioxide ($CO_2$) monitoring system 100 according to an example embodiment. Carbon dioxide monitoring system 100 may include a $CO_2$ measuring and restoration ("CMR") unit 110, an oxygen source 120, an oxygen flow re-shaper (OFR) 130, and a respiration (oxygen) mask 140. The oxygen flow re-shaper 130 may receive $O_2$ from the oxygen source 120, for example at a known, or predetermined, flow rate and may output an input oxygen flow 142 to the mask 140 in the form of, for example, high-frequency oxygen pulses (high-frequency oxygen flow). The oxygen flow re-shaper 130 may be configured to receive an oxygen flow from the oxygen source 120, and to control, adjust or modify characteristics of the inflow oxygen such that the oxygen flow re-shaper 130 outputs, for the mask 140, an input oxygen flow 142 that is useful both for the patient breathing it and for the oxygen signal cancellation process.

Exhaled $CO_2$ flow 144 is also provided to the mask 140 during respiration. The mask 140, therefore, receives both high-frequency oxygen (e.g., the input oxygen flow 142) and the exhaled $CO_2$ 144, and, therefore, the exhaled $CO_2$ 144 is diluted, in the mask 140, by high-frequency input oxygen flow 142.

The carbon dioxide measuring and restoration unit 110 measures $CO_2$ concentration, or $CO_2$ partial pressure, as diluted by oxygen, and restores the oxygen-diluted $CO_2$ to the original concentration of the exhaled $CO_2$ 144. Restoration of the concentration of the exhaled $CO_2$ 144 may include, for example, restoration of the shape, frequency, and magnitude of the concentration level of the exhaled $CO_2$. The carbon dioxide measuring and restoration unit 110 may include a gas sampling chamber ("GSC") 150 for receiving or drawing (for example continually or periodically) the gas samples 146 from the mask 140. The carbon dioxide measuring and restoration unit 110 may also include a $CO_2$ restoration unit ("CRU") 160 for restoring the $CO_2$ measurements. The term "restoration," as used herein, is intended to denote adjustment or modification of a measured (detected) $CO_2$ concentration level to a value that genuinely represents, indicates, or resembles a concentration level of the originally (non-diluted) exhaled $CO_2$. The amount of $CO_2$ concentration adjustment or modification may be determined based on the oxygen 142 provided to the mask 140, and also based on measured characteristics (e.g., concentration level) of the oxygen admixture. The gas samples 146 that the GSC 150 receives, or draws, from the mask 140 include a gas mixture that includes diluted $CO_2$ and the diluting oxygen. The gas mixture is expressed herein as $CO_2$(s)+$O_2$(n), where (s) denotes a "signal" (or data) that represents the diluted (impaired) $CO_2$ signal whose original (non-diluted) concentration level is to be restored, and (n) denotes oxygen admixture ("noise") causing the $CO_2$ dilution. The $O_2$ in the mask 140, hence in the GSC 150, is, in turn, diluted by $CO_2$, but it is of no clinical interest because $O_2$ is provided to the mask 140 in a way that enables the subject wearing the mask 140 to breathe as efficiently as possible. In addition, knowing characteristics (e.g., concentration level) of the oxygen admixture vis-à-vis characteristics of the $O_2$ provided to the mask 140 facilitates determination of the concentration level of the $CO_2$ admixture in each gas sample.

In some embodiments, the GSC 150 may include two, separate, gas cells—one gas cell for detecting exhaled $CO_2$ samples and another gas cell for detecting $O_2$ samples. Each gas cell may include, or have associated with it, a respective gas detector. The embodiments disclosed herein include detecting a $CO_2$ and $O_2$ admixture, and using characteristics of the $O_2$ provided to the mask 140 to both cancel the $O_2$ 'component' in the $CO_2/O_2$ gas mixture and restoring characteristics of the originally (non-diluted) exhaled $CO_2$. Therefore, using two, separate, gas cells to detect $CO_2$ and $O_2$ may include dealing with 'out-of-phase' and 'out-of-synchronization' measurement issues with regard to the detection of the two gases. For example, if the two-cell measurement option is used, the two gas samples (one in the $CO_2$ cell, the other in the $O_2$ cell) should be kept under the same physical conditions (e.g., in terms of pressure, a size of the gas sample, a flow rate, and a temperature) and/or be measured simultaneously. This may be useful because, for example, a concentration of gas in a gas mixture is measured by its partial pressure, and to obtain reliable results, $CO_2$ restoration requires that the two partial pressures (one of the $CO_2$, another of the $O_2$) be related to (e.g., measured in) the same gas sample and at the same time.

In our case, measuring concentration of $CO_2$ in a $CO_2/O_2$ gas sample includes measuring the partial pressure of $CO_2$ in the $CO_2/O_2$ gas sample, and measuring concentration of $O_2$ includes measuring the partial pressure of $O_2$ in the $CO_2/O_2$ gas sample. Therefore, measuring $CO_2$ and $O_2$ in separate gas samples may skew the $CO_2$ and $O_2$ readings and, thus, result in unreliable restoration of the non-diluted concentration level of the exhaled $CO_2$. Therefore, preferably, the GSC 120 may, in some embodiments, include one, common, gas cell that is designed to facilitate simultaneous detection of both the $CO_2$ admixture (sample) and the $O_2$ admixture (sample) in the same gas sample.

The GSC 150 may include a $CO_2$ detector 152 and an oxygen detector 154. The carbon dioxide detector 152 and the $O_2$ detector 154 may be configured such that they can detect $CO_2$ and $O_2$, respectively, in the same gas cell (hence in the same gas sample) at the same time, which is beneficial for the oxygen 'noise' cancellation and $CO_2$'s concentration level restoration process. Each detector 152, 154 may output, in real-time, an analog signal that represents a concentration level (e.g., expressed as partial pressure) of the respective gas. For example, the $CO_2$ detector 152 may generate an output 156 that includes an analog signal P_co2(t) that represents the partial pressure of the $CO_2$ in the $CO_2/O_2$ gas sample, and the $O_2$ detector 154 may generate an output 158 that includes an analog signal P_o2(t) that represents the partial pressure of $O_2$ in the $CO_2/O_2$ gas sample. Rather than outputting analog signals, the $CO_2$ detector 152 and the $O_2$ detector 154 may output digital data that represent the partial pressure of $CO_2$ in the $CO_2/O_2$ gas sample and the partial pressure of $O_2$ in the $CO_2/O_2$ gas sample, respectively The CRU 160 may receive signals P_co2(t) and P_o$_2$(t). In addition, the CRU 160 may receive a signal (or data) 132, O2(A,F) that represents characteristics of the high-frequency $O_2$ that is provided to the mask 140. A in O2(A,F) represents amplitude of the $O_2$, F in O2(A,F) represents the frequency of the $O_2$. The term "high-frequency oxygen," as used herein, is intended to denote $O_2$ that is provided to the mask 140 at high frequency. The term "high-frequency," as used herein, is intended to denote a frequency that is sufficiently high to facilitate distinction between oxygen admixture in the oxygen-diluted $CO_2$ mixture and the $CO_2$ admixture in the oxygen-diluted $CO_2$ mixture by means of an ANC (e.g., the ANC 166) or by digital signal processing, and the like. The frequency at which $O_2$ may be provided to the mask 140 may be selected based on the normal respiration rate (breathes per minute, "BPM"), which is between 12 and 25 BPM. Accordingly, the $O_2$ that is provided to the mask 140 at a frequency which is, for example, at least ten times the average BPM may be regarded as high-frequency oxygen. For example, the $O_2$ that is provided to the mask 140 at a rate of, for example, 300 times per minute may be regarded as high-frequency oxygen. Generally, the more efficient (e.g., the more 'sensitive') the ANC, digital signal processing (DSP), etc., is in terms of detection of the $O_2$ signal/data in the oxygen-diluted $CO_2$ signal/data, the lower the "high-frequency" can be. In some examples, the frequency at which $O_2$ is provided to a mask may be within the range of 5 Hz to 10 Hz. As should be appreciated, other frequency ranges may also be used.

The CRU 160 may include a processor 162 and an adaptive noise canceller ("ANC") 166. ANC 166 may receive signals 156 and 158 that respectively represent the partial pressure of the measured $CO_2$ and $O_2$. In addition, the ANC 166 may receive the signal 132. The processor 162 may initially calculate a coefficient matrix for of the ANC 166, and the ANC 166 may apply the coefficient matrix to the signals 156, 158, and 132. The ANC 166 may generate an output 164 that includes a signal $\widehat{CO}_2$ (ŝ) that represents a restored $CO_2$ concentration level, and the processor 162 may iteratively recalculate the coefficient matrix for or of the ANC 166 in order for the ANC 166 to minimize, in each iteration, an error value that represents a difference between characteristics of the high-frequency oxygen (per the signal 132) and characteristics of the $O_2$ admixture as measured by the $O_2$ detector 154.

The ANC 166 may iteratively minimize the error value, for example, until the error value is smaller than a predetermined threshold value. In general, the smaller the error value, the closer the $CO_2$ concentration level, which is represented by the ANC's output signal $\widehat{CO}_2$ (ŝ) at 164 to the sought for concentration level of the exhaled $CO_2$ 144. The Signal $\widehat{CO}_2$ (ŝ) 164 may be displayed on a computer display 102. The display 102 shows, at 170, restored (non-diluted) $CO_2$ concentration (in mmHg) during three respiration cycles.

In some embodiments, a system for monitoring a concentration level of the exhaled $CO_2$ may include a GSC identical or similar to the GSC 150, which receives gas samples from a mask identical or similar to 140 attached to a face of a subject. Each gas sample may include an oxygen admixture that originates from an input oxygen flow, such as input oxygen flow 142, provided to the mask, and, in addition, $CO_2$ that is exhaled by the subject into the mask. The system may also include a $CO_2$ detector identical or similar to the $CO_2$ detector 152 to detect a concentration level of $CO_2$ in the gas sample, and an oxygen detector identical or similar to the oxygen detector 154 to detect a concentration level of oxygen admixture in the gas sample. The system may also include a CRU identical or similar to the CRU 160 to restore a concentration level of the $CO_2$ exhaled (144) by the subject based on characteristics of the input oxygen flow (e.g., the input oxygen flow 142) and the concentration level of the oxygen admixture detected in the gas sample. The system may also include a computer display (e.g., the computer display 102) to display a signal (e.g., the signal 170) that represents the restored concentration level of the exhaled $CO_2$ (e.g., $CO_2$ 144).

The $CO_2$ detector (e.g., the detector 152) and the oxygen detector (e.g., the detector 154) may respectively be configured to simultaneously detect $CO_2$ and oxygen in a same gas sample. For example, if the gas sample flows in a first direction, one detector may be disposed (oriented) in a second direction that is at a first angle relative to the first direction, and the other detector may be disposed (oriented) in a third direction that is at a second angle relative to the first and second directions. The first and second angles may be 90 degrees. Other angles may be selected for the first angle, the second angle, or both angles.

Figure 2:
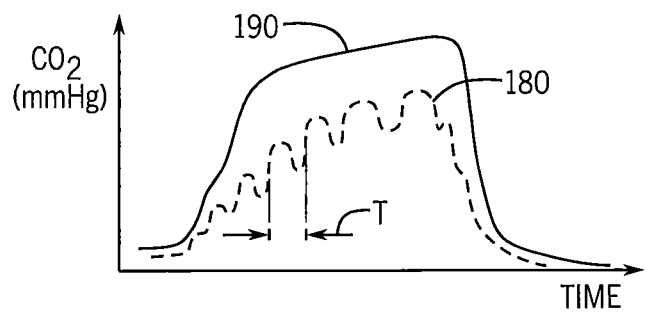
FIG. 2 shows a comparative graph, in accordance with an embodiment of the present disclosure.

FIG. 2 shows a graph that demonstrates the dilution effect of the high-frequency input oxygen flow 142 on the exhaled $CO_2$ 144. The graph shows a $CO_2$ signal 180 (measured in pressure units, mmHg) after it is impaired by the diluting high-frequency input oxygen flow 190. As shown in FIG. 2, the high-frequency oxygen flow 190, having a pulse frequency F (F=1/T), is shown superimposed on the $CO_2$ signal 180. Another effect of the diluting oxygen on the $CO_2$ measurements is, per the description herein with regard to gases partial pressure, that the magnitude of the $CO_2$ is generally lower than it should be (e.g., lower than the amplitude of the exhaled $CO_2$ at the subject's nostrils), due to the dilution effect of input oxygen flow 190.

Figure 3:
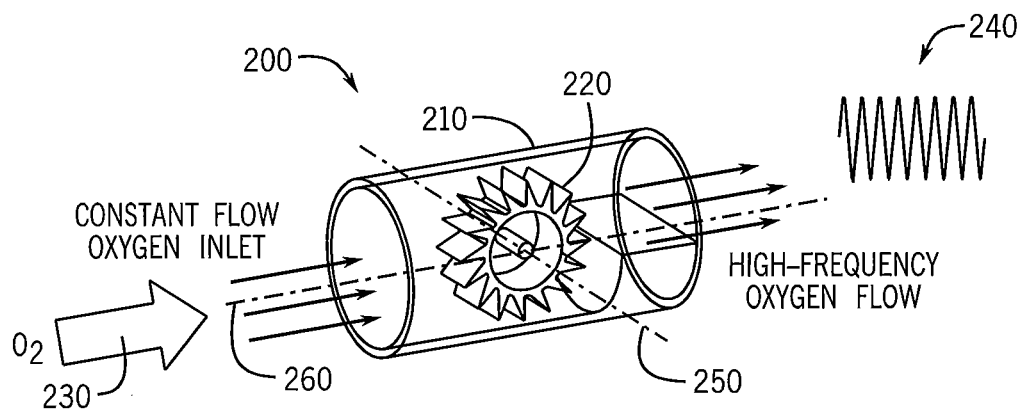
FIG. 3 depicts an oxygen flow re-shaper, according to an embodiment of the present disclosure.

FIG. 3 schematically illustrates an oxygen flow re-shaper (OFR) 200, according to an embodiment of the present disclosure. The OFR 200 may include a tube 210 through which oxygen can flow from an oxygen source to an oxygen mask (e.g., the mask 140), and a toothed wheel, which is schematically shown at 220, to control the oxygen gas dynamics in the tube 210. The tube 210 includes an oxygen intake portion into which oxygen 230 flows at a constant flow rate, and an oxygen outlet portion from which high-frequency oxygen 240 flows out to an oxygen mask (e.g., to the mask 140). The toothed wheel 220 is designed in terms of, for example, number, size, shape and angular spacing of the teeth, such that $O_2$ flowing through the tube 210 causes the toothed wheel 220 to rotate around a rotation axis 250 of the toothed wheel 220, to thereby generate the high-frequency oxygen flow 240. During rotation of the toothed wheel 220 the toothed wheel 220 introduces a cycling resistance to the oxygen flow that results in the cyclically changing oxygen flow. Rotation axis 250 of the toothed wheel 220 is perpendicular to a longitudinal axis 260 of the tube 210 (to the direction of the oxygen flow in the tube 210).

Figure 4:
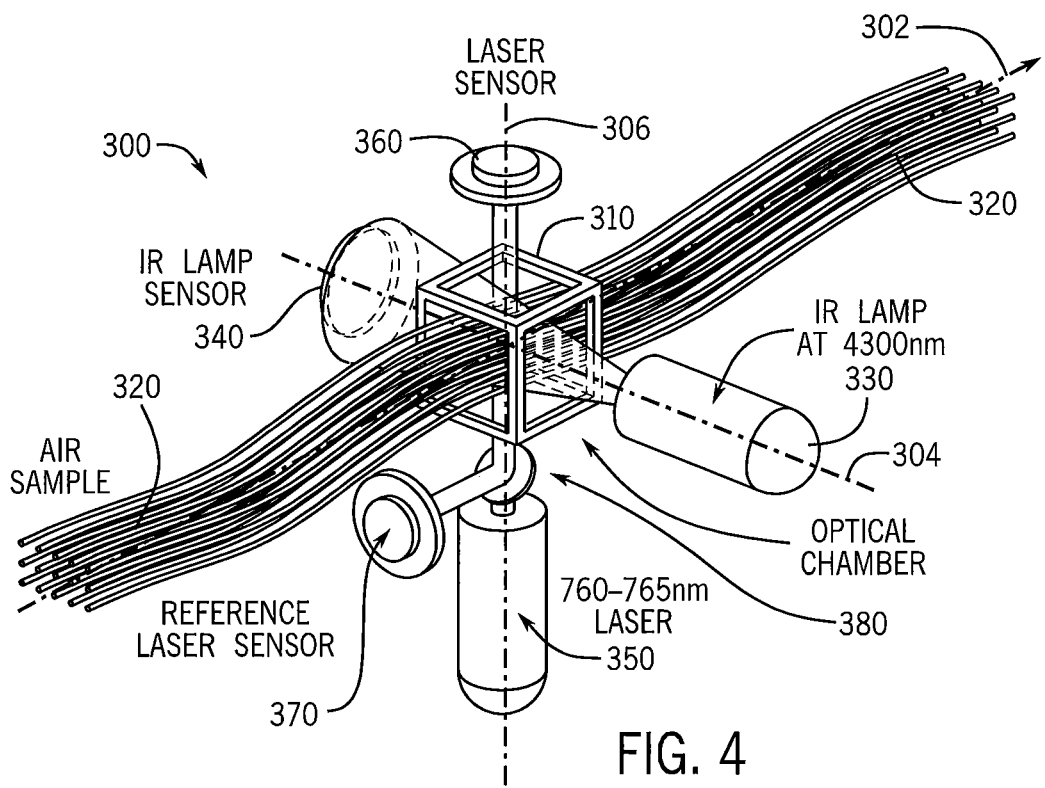
FIG. 4 shows a $CO_2/O_2$ detector, according to an embodiment of the present disclosure.

FIG. 4 is a schematic $CO_2/O_2$ detector 300, according to an example embodiment. The $CO_2/O_2$ detector 300 includes a gas sampling cell (GSC) 310 through which gas sample 320 flows. The $CO_2/O_2$ detector 300 also includes a $CO_2$ detector and an $O_2$ detector. The $CO_2/O_2$ detector 300 enables simultaneous measurement of the $CO_2$ and $O_2$ admixtures in the same gas sample (e.g, in the same gas mixture), which, as described herein, is beneficial to the $CO_2$ restoration process.

The $CO_2$ detector may include an infrared (IR) lamp 330 to irradiate IR light (e.g., with 4,300 nm wavelength) into and through the GSC 310, and an IR light sensor 340 to sense IR light that passes through the GSC 310 (e.g., through the gas sample). The higher the $CO_2$ concentration, or partial pressure, in the gas mixture (gas sample) in the GSC 310, the lower the intensity of the IR light that impinges on the IR light sensor 340.

The $O_2$ detector may include a laser source 350 to emit a laser beam (e.g., with 760-765 nm wavelength) into and through the GSC 310, and a laser sensor 360 to sense the laser light that passes through the GSC 310. The higher the $O_2$ concentration, or partial pressure, in the gas mixture (gas sample) in the GSC 310, the lower the intensity of the laser light that impinges on the laser sensor 360. The $O_2$ detector may also include a reference laser sensor 370 (e.g., to increase the $O_2$ detection accuracy) and a semi-transparent mirror 380 that enables some of the laser light originating from the laser source 350 to pass through it, towards (the main) laser sensor 360, but it also deflects a portion of the laser light to the reference laser sensor 370.

The carbon dioxide detector 152 and the oxygen detector 154 may respectively be assembled onto the GSC 310 to enable detection of the $CO_2$ and $O_2$ in the same gas sample at the same time. Each measured $CO_2$ concentration value, thus, has a conjugated oxygen measured concentration value. For example, if gas (air) sample 320 flows in direction 302, the $CO_2$ detector 330 and the $CO_2$ sensor 340 may be disposed on opposite sides of the GSC 310 and form a line 304 (a '$CO_2$ measuring line or axis') that may be, for example, perpendicular to gas (air) flow direction 302. The oxygen detector 350 and the $O_2$ sensor 360 may also be disposed on opposite sides of the GSC 310 and form a line 306 (e.g., an 'oxygen measuring line or axis') that may be, for example, perpendicular to the gas (air) flow direction 302 and to the $CO_2$ measuring line 304. The $CO_2$ measuring line 304 and the oxygen measuring line 306 may form a plane that may be perpendicular to, or be at other angles, relative to the gas flow direction 302. The angles between $CO_2$ measuring line 304, the $O_2$ measuring line 306, and the gas (air) flow direction 302 may be 90 degrees, though other angles may be selected.

Figure 5:
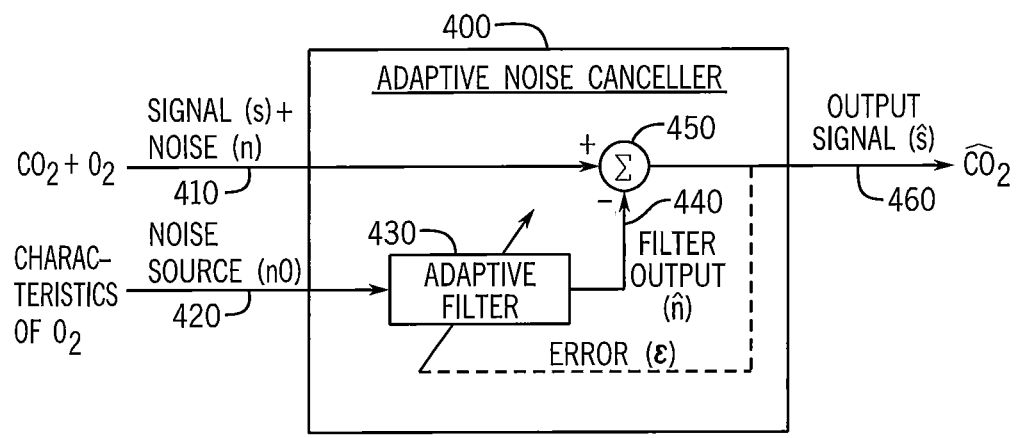
FIG. 5 schematically illustrates an adaptive noise canceller ("ANC"), according to an embodiment of the present disclosure.

FIG. 5 shows an adaptive noise canceller (ANC) 400, according to an embodiment of the present disclosure. The ANC 160 of FIG. 1 may operate in a similar way as the ANC 400. The ANC 400 includes a primary input 410 and a reference input 420. The primary input 410 receives a signal s from a signal source that is corrupted by the presence of noise n. The signal s and the noise n are uncorrelated. The reference input 420 receives a noise n0 that is uncorrelated with the signal s, but is correlated in some way with the noise n. The noise n0 (at 420) passes through an adaptive filter 430 to produce an output n̂ (at 440) that is a close estimate of the input noise n in the primary input 410. The noise estimate n̂ (440) is subtracted (at 450) from the corrupted signal (s+n) 410 to produce an estimate ŝ (460), which is the output of the ANC 400.

In noise canceling systems, a practical objective is to produce a system output ŝ=(s+n)−n̂ that is a best fit (e.g., in the least squares sense) to the signal s. This objective is accomplished by feeding the system output ŝ back to the adaptive filter, and adjusting the filter by using, for example, a least mean square (LMS) adaptive algorithm that minimizes the total system output power. In other words, the system output can serve as an error signal for the adaptive process.

For the ANC 400, the signal power of the signals ŝ (ŝ=s+n−n̂) is given in the following equation:

$$\hat{s}^2 = s^2 + 2s(n-\hat{n}) + (n-\hat{n})^2$$

Taking expectation of both sides and realizing that s is uncorrelated with n0 and n̂, $$E[\hat{s}^2] = E[s^2] + 2E[s(n-\hat{n})] + E[(n-\hat{n})^2]$$

Since the filter is adjusted to minimize $E[\hat{s}^2]$, the signal power itself $E[s^2]$ is unaffected by the minimization process. That is:

$$\min E[\hat{s}^2] = E[s^2] + \min E[(n-\hat{n})^2]$$

Thus, when the filter is adjusted to minimize the output noise power $E[\hat{s}^2]$, the output noise power $(n-\hat{n})^2$ is also minimized. Since the signal in the output remains constant, minimizing the total output power maximizes the output signal-to noise ratio. Since (ŝ−s)=(n−n̂), this is equivalent to causing the output ŝ to be a best least squares estimate of the signal s.

By analogy, according to some embodiments of the present disclosure, the corrupted signal (s+n) at the primary input 410 of the ANC 400 denotes the impaired (diluted) $CO_2$ admixture in a gas mixture or sample, and the noise signal n0 at the reference input 420 of the ANC 400 denotes a signal, or data, that represents characteristics of the high-frequency oxygen flow that dilutes the $CO_2$ in the mask. First data, which represents both the $CO_2$ and the oxygen admixture in the gas sample, may be provided to the input 410 (a "first input") of the ANC 400, and, at the same time, second data, which represents characteristics of the input oxygen flow, may be provided to the input 420 (a "second input") of the ANC 400. The ANC 400 may use the first and the second data to cancel, in real-time, the oxygen noise signal that represents the oxygen admixture in the gas samples, and, while cancelling the oxygen noise signal, to output the restored concentration level of the $CO_2$ exhaled by the subject. As described herein in connection with gas partial pressure in a gas mixture, given a constant pressure of a two-gas mixture, the lesser the partial pressure of one gas admixture, the greater the partial pressure of the other gas admixture. Therefore, the greater the cancellation of the signal that represents the oxygen admixture in a gas sample/mixture is, the greater the partial pressure of the $CO_2$ admixture would be. The maximum concentration level to which the $CO_2$ can reach (e.g., can be restored to) as a result of the oxygen cancellation process is the exhaled $CO_2$'s original concentration level (e.g., the concentration level of the exhaled $CO_2$ before it is diluted by oxygen in the mask).

As seen above, the adaptive noise canceller works on the principle of correlation cancellation (e.g., the ANC output contains the primary input signals, with the component, whose correlated estimate is available at the reference input, removed). Therefore, the ANC is capable of removing (from the corrupted signal) only noises which are correlated with the noises at the reference input.

Figure 6:
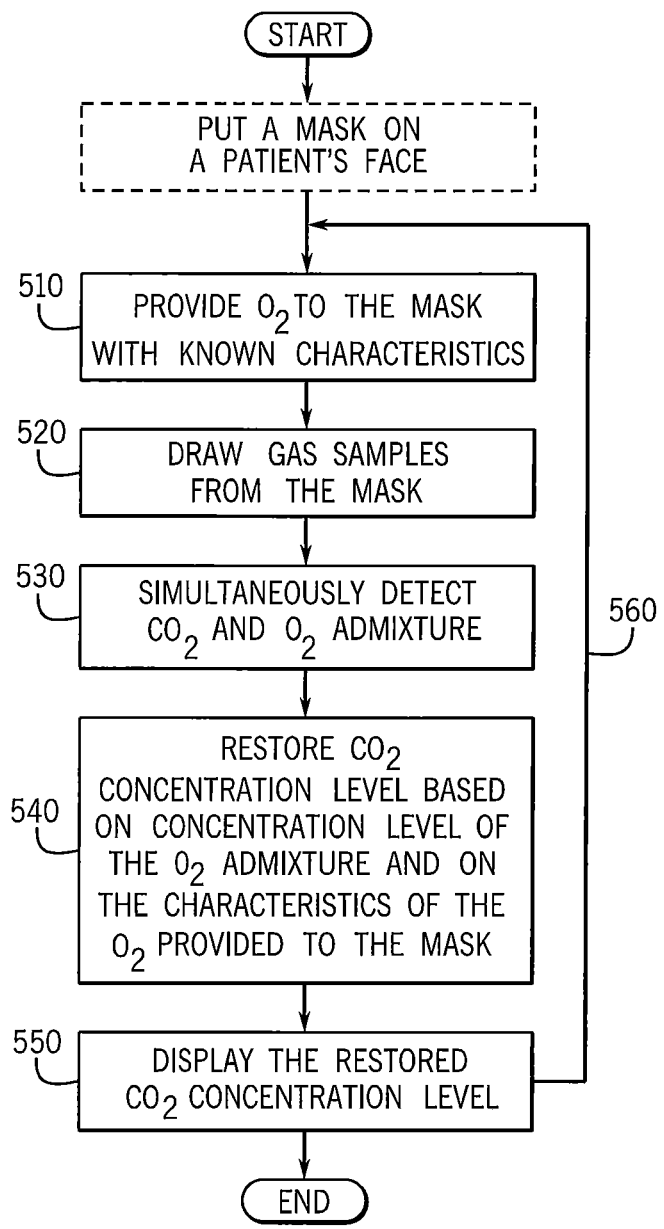
FIG. 6 is a flow diagram of a method of restoring exhaled carbon dioxide concentration level using the $CO_2$ monitoring system of FIG. 1, according to an embodiment of the present disclosure.

FIG. 6 shows a method of restoring exhaled carbon dioxide concentration level, according to an embodiment of the present disclosure. FIG. 6 is described below in association with FIG. 1. In step 510, the input oxygen flow 142 is provided to the mask 140 attached to a subject. Characteristics of the input oxygen flow 142 may be known. For example, characteristics of the input oxygen flow 142 may be predetermined, for example by presetting parameter(s) of the input oxygen flow (e.g., frequency, amplitude, flow rate, etc.) and maintaining the preset parameter(s) throughout the entire $CO_2$ monitoring procedure. Additionally or alternatively, the characteristics of the input oxygen flow 142 may be determined by measuring them in real-time as oxygen continues to be provided to the mask 140. Steps 520 through 550, which are described below, may be performed by the CMR unit 110 (or by a similar system) that may be part of the $CO_2$ monitoring system 100 (or part of a similar system).

In step 520, the CMR unit 110, which monitors carbon dioxide exhaled by the subject during a respiration cycle (in, for example, a series of consecutive respiration cycles), receives or draws gas sample(s), shown at 146, from the mask 140. Each gas sample (a gas mixture) may include a $CO_2$ sample and, in addition, an $O_2$ admixture sample that originates from, and is characteristically (characteristic-wise) related to, the input oxygen flow 142. The CMR unit 110 may receive or draw gas samples from the mask 140 continuously, or periodically (e.g., according to a predetermined interval), or intermittently, or once in a while.

In step 530, the CMR unit 110 may simultaneously detect a concentration level of the $CO_2$ sample and a concentration level of the $O_2$ admixture sample in each gas sample 146. In step 540, the CMR unit 110 may restore (e.g., estimate) a concentration level of the $CO_2$ sample exhaled by the subject during the respiration cycle, based on characteristics of the input $O_2$ flow 142 existing at the time when (that is, to be in temporal synchronization with the time at which) the concentration level of the $CO_2$ sample and the concentration level of the $O_2$ sample are detected by the GSC 150, and also based on the concentration level of the $O_2$ admixture detected in the same gas sample. The same restoration process may be repeated 560 for subsequent respiration cycles.

In step 550, the CMR unit 110 may output 164, to a computer system, a signal or data that represents the restored (e.g., estimated non-diluted) concentration level of exhaled $CO_2$ concentration for the respiration cycle, and, if required, for subsequent respiration cycles. The computer may process the signal or data that represents the restored concentration level of exhaled $CO_2$ concentration and, based on the processing, the computer may introduce clinical data that is related to the restored concentration level of exhaled $CO_2$. The computer may additionally or alternatively display the concentration level of the exhaled $CO_2$ 170 on the computer display 102 over time. The steps described above may similarly be repeated 560 for subsequent gas samples 146 in a same respiration cycle, and, if required, the steps described above may similarly be repeated 560 for subsequent respiration cycles.

Restoring the concentration level of $CO_2$ sample 144 exhaled by the subject during a respiration cycle may include modification of the concentration level of the $CO_2$ sample that the GSC 150 detects in the gas sample/mixture 146. Restoring the concentration level of exhaled $CO_2$ 144 may include determining and using characteristics of the input oxygen flow 142. Determining the characteristics of the input oxygen flow 142 may include setting, or predetermining, characteristics (e.g., a parameter) of the input oxygen flow 142 and maintaining the predetermined characteristics of the input oxygen flow 142 while exhaled $CO_2$ is being monitored (e.g., measured). Determining the characteristics of the input oxygen flow 142 may include measuring a parameter of the input oxygen flow 142. The parameter of the input oxygen flow 142 may be selected from a group consisting of: a frequency at which the input oxygen flow is provided to the mask 140, and an amplitude of the input oxygen flow 142. Both the frequency and amplitude parameters may be used, rather than using one of the frequency or amplitude parameter.

Detecting the concentration level of the $CO_2$ sample and the concentration level of the oxygen admixture in the gas sample 146 may include: (i) providing the gas sample 146, or a portion of the gas sample 146, to the GSC 150, and (ii) simultaneously detecting both the concentration level of the $CO_2$ and the oxygen admixture in the gas sample 146 contained in the GSC 150.

Restoring the concentration level of the exhaled $CO_2$ 144 may include cancelling an oxygen 'noise' signal representing the oxygen admixture in the gas sample 146. Cancelling the oxygen noise signal or data may be effected by the ANC 166. Using the ANC 166 may include changing a set of coefficients of the ANC 166. The set of coefficients of the ANC 166 may be changed based on a signal or data at the output of the ANC 166.

Cancelling the oxygen noise signal by the ANC 166 may include: (i) providing first data (at 410) representing a superposition of the $CO_2$ and oxygen admixture in the gas sample 146 to a first input 410 (e.g., a "primary" input) of the ANC 166; (ii) providing second data (at 420) representing the characteristics of the input oxygen flow 142 to a second input 420 (e.g., a "reference" input) of the ANC 166; and (iii) using (based on) the first and second data, adjusting the set of coefficients of the ANC 166 so as to cause the ANC 166 to restore a concentration level of the $CO_2$ exhaled by the subject, and to output the restored concentration level of the $CO_2$ exhaled by the subject.

The methods described herein may further include a step of calibration of the CMR unit 110. The calibration process may include: (i) providing to the mask 140 only the input oxygen flow 142 and detecting an oxygen dispersion (concentration) level in the gas sample, and/or providing to the mask 142 only the exhaled $CO_2$ 144 and detecting $CO_2$ concentration level in the gas sample in order to estimate a $CO_2$ rebreathing; and (iii) setting parameters of the input oxygen flow 142 based on the oxygen dispersion level and/or based on the estimated $CO_2$ rebreathing.

Various aspects of the various embodiments disclosed herein are combinable with other embodiments disclosed herein. Although portions of the discussions herein may relate to a particular method of restoring $CO_2$ level of exhaled $CO_2$, embodiments of the disclosure are not limited in this regard, and may include, for example, using various digital signal processing ("DSP") algorithms or techniques, etc.

Although portions of the discussions herein may relate to a particular type of ANC, the present disclosure is not limited in this regard, and may include other types of ANCs, or the like. Those skilled in the art of signal processing will understand how to implement the ANC to restore the genuine concentration level of exhaled $CO_2$, and will readily appreciate that numerous changes, variations, and modifications, for example to the ANC and to the $CO_2/O_2$ common sampling cell and to $CO_2/O_2$ detectors, can be made without departing from the scope of the disclosure.

The invention claimed is:

1. A method of restoring an exhaled carbon dioxide ($CO_2$) concentration level, comprising:
   providing an input oxygen flow to a mask attached to a subject;
   using, a $CO_2$ monitoring system configured to monitor $CO_2$ exhaled by the subject into the mask during a respiration cycle, to perform the steps of:
      drawing, from the mask, a gas sample including exhaled $CO_2$ and oxygen ($O_2$) admixture originating from the input oxygen flow;
      detecting, in the gas sample, a concentration level for the $CO_2$ and for the $O_2$ admixture; and
      restoring a concentration level of the $CO_2$ as exhaled by the subject during the respiration cycle based on characteristics of the input oxygen flow and the concentration level of the oxygen admixture detected in the gas sample, wherein restoring the concentration level of the exhaled $CO_2$ comprises determining the characteristics of the input oxygen flow based on a set parameter and/or on a measured parameter; and
   displaying, on a computer display, for the respiration cycle, a signal representing the restored concentration level of the exhaled $CO_2$.

2. The method of claim 1, wherein restoring the concentration level of the $CO_2$ exhaled by the subject during the respiration cycle comprises modifying the concentration level of the $CO_2$ detected in the gas sample.

3. The method of claim 1, wherein detecting the concentration level of the $CO_2$ and the concentration level of the $O_2$ admixture in the gas sample comprises: providing the gas sample, or a portion of the gas sample, to a common gas sampling chamber, and simultaneously detecting both the concentration level of the $CO_2$ and $O_2$ admixture in the gas sample contained in the common gas sampling chamber.

4. The method of claim 1, wherein determining the characteristics of the input oxygen flow comprises setting the set parameter of the input oxygen flow and maintaining the set parameter of the input oxygen flow, wherein the set parameter comprises a frequency at which the input oxygen flow is provided to the mask, an amplitude of the input oxygen flow, or a combination thereof.

5. The method of claim 1, wherein determining the characteristics of the input oxygen flow comprises measuring the measured parameter of the input oxygen flow, wherein the measured parameter comprises a frequency at which the input oxygen flow is provided to the mask, an amplitude of the input oxygen flow, or a combination thereof.

6. The method of claim 1, wherein restoring the concentration level of the exhaled $CO_2$ comprises cancelling an oxygen noise signal representative of the $O_2$ admixture in the gas sample.

7. The method of claim 6, wherein cancelling the oxygen noise signal comprises using an adaptive noise canceller.

8. The method of claim 7, wherein using the adaptive noise canceller comprises changing coefficients of the adaptive noise canceller based on a signal or data output by the adaptive noise canceller.

9. The method of claim 8, wherein cancelling the oxygen noise signal comprises:
providing first data representing both the $CO_2$ and the $O_2$ admixture in the gas sample to a first input of the adaptive noise canceller;
providing second data representing the characteristics of the input oxygen flow to a second input of the adaptive noise canceller; and
cancelling the oxygen noise signal that represents the $O_2$ admixture in the gas sample by using the first and second data.

10. The method of claim 9, comprising calibrating the $CO_2$ monitoring system, the calibrating comprising: providing to the mask only an initial input oxygen flow and detecting an oxygen dispersion level in a respective gas sample and setting parameters of the input oxygen flow based on the oxygen dispersion level and/or providing to the mask only exhaled $CO_2$ and detecting an initial $CO_2$ concentration level in a respective gas sample in order to estimate $CO_2$ rebreathing and setting parameters of the input oxygen flow based on the estimated $CO_2$ rebreathing.

11. A system configured to monitor an exhaled carbon dioxide ($CO_2$) concentration level, comprising:
a gas sampling chamber configured to receive a gas sample from a mask attached to a face of a subject, the gas sample including an oxygen ($O_2$) admixture originating from an input oxygen flow provided to the mask and $CO_2$ exhaled by the subject into the mask;
a $CO_2$ detector configured to detect a concentration level of $CO_2$ in the gas sample;
an $O_2$ detector configured to detect a concentration level of $O_2$ admixture in the gas sample;
a $CO_2$ restoration unit configured to determine a restored concentration level of the $CO_2$ exhaled by the subject based on characteristics of the input $O_2$ flow and the concentration level of the $O_2$ admixture detected in the gas sample; and
a computer display configured to display a signal representing the exhaled $CO_2$ with the restored concentration level.

12. The system of claim 11, wherein the $CO_2$ detector and the $O_2$ detector are, respectively, configured to simultaneously detect $CO_2$ and $O_2$ in a same gas sample.

13. The system of claim 11, wherein the $CO_2$ restoration unit comprises an adaptive noise canceller.

14. The system of claim 11, comprising an $O_2$ flow re-shaper configured to receive an $O_2$ flow from an $O_2$ source and to control the characteristics of the inflow $O_2$ so as to output to the mask the input oxygen flow.

15. The system of claim 11, comprising the mask.

16. A system configured to monitor a non-diluted concentration level of carbon dioxide ($CO_2$), comprising:
a gas sampling chamber configured to receive a dilute $CO_2$ gas sample from a mask attached to a face of a subject, wherein the dilute $CO_2$ gas sample comprises a mixture of an oxygen ($O_2$) admixture and $CO_2$, and wherein the $CO_2$ is exhaled by the subject during a respiration cycle;
a $CO_2$ detector disposed within the gas sampling chamber and configured to detect $CO_2$ in the dilute $CO_2$ gas sample;
an $O_2$ detector disposed within the gas sampling chamber and configured to detect the $O_2$ admixture in the dilute $CO_2$ gas sample; and
a $CO_2$ restoration unit comprising a processor configured to monitor a concentration level of the $CO_2$ and a concentration level of the $O_2$ admixture in the dilute $CO_2$ gas sample and to determine the non-diluted concentration level of $CO_2$ as exhaled by the subject during the respiration cycle based on characteristics of a flow of $O_2$ into the mask and the concentration level of $O_2$ admixture detected in the dilute $CO_2$ gas sample.

17. The system of claim 16, wherein the processor is configured to modify the concentration level of the $CO_2$ detected in the dilute $CO_2$ gas sample to determine the non-diluted concentration level of $CO_2$.

18. The system of claim 16, comprising an adaptive noise canceller configured to cancel an oxygen noise signal representative of the $O_2$ admixture in the dilute $CO_2$ gas sample to determine the non-diluted concentration level of the $CO_2$.

19. The system of claim 16, wherein the characteristics of the flow of $O_2$ comprises measuring a parameter of the flow, the parameter comprises a frequency at which the flow of $O_2$ is provided to the mask, an amplitude of the flow of $O_2$, or a combination thereof.

* * * * *